(12) United States Patent
Freiman et al.

(10) Patent No.: US 12,396,698 B2
(45) Date of Patent: Aug. 26, 2025

(54) APPARATUS FOR GENERATING PHOTON COUNTING SPECTRAL IMAGE DATA

(71) Applicant: KONINKLIJKE PHILIPS N.V., Eindhoven (NL)

(72) Inventors: Mordechay Pinchas Freiman, Zichron-Yaakov (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 511 days.

(21) Appl. No.: 17/781,142

(22) PCT Filed: Dec. 16, 2020

(86) PCT No.: PCT/EP2020/086570
§ 371 (c)(1),
(2) Date: May 31, 2022

(87) PCT Pub. No.: WO2021/122843
PCT Pub. Date: Jun. 24, 2021

(65) Prior Publication Data
US 2022/0409159 A1    Dec. 29, 2022

(30) Foreign Application Priority Data

Dec. 16, 2019    (EP) .................................. 19216582

(51) Int. Cl.
*G06V 10/82*    (2022.01)
*A61B 6/00*    (2006.01)
(Continued)

(52) U.S. Cl.
CPC ............ *A61B 6/5211* (2013.01); *G06N 3/045* (2023.01); *G06N 3/08* (2013.01); *G06V 10/82* (2022.01);
(Continued)

(58) Field of Classification Search
CPC .............. G06V 10/82; G06V 2201/034; G06T 2207/30004
See application file for complete search history.

(56) References Cited

U.S. PATENT DOCUMENTS

| 2012/0224760 A1 | 9/2012 | Goshen |
| 2018/0276802 A1 | 9/2018 | Lichy |

(Continued)

FOREIGN PATENT DOCUMENTS

| WO | WO2019141527 A1 | 7/2019 |
| WO | WO2019149762 A1 | 8/2019 |

OTHER PUBLICATIONS

PCT International Search Report, International application No. PCT/EP2020/086570, Mar. 18, 2021.

(Continued)

*Primary Examiner* — Ming Y Hon
(74) *Attorney, Agent, or Firm* — Larry Liberchuk

(57) ABSTRACT

The present invention relates to an apparatus (10) for generating photon counting spectral image data, comprising: an input unit (20); a processing unit (30); and an output unit (40). The input unit is configured to receive non-photon counting X-ray spectral energy data. The processing unit is configured to implement a deep learning regression algorithm to generate photon counting X-ray spectral data, and the generation comprises utilization of the non-photon counting X-ray spectral energy data. The output unit is configured to output the photon counting X-ray spectral data.

14 Claims, 4 Drawing Sheets

(51) Int. Cl.
*G06N 3/045* (2023.01)
*G06N 3/08* (2023.01)
(52) U.S. Cl.
CPC .......... *G06T 2207/30004* (2013.01); *G06V 2201/034* (2022.01)

(56) References Cited

U.S. PATENT DOCUMENTS

2018/0374209 A1* 12/2018 Patil ............... G06N 3/084
2019/0150864 A1* 5/2019 Flohr .............. G06T 5/70
2019/0251713 A1* 8/2019 Chen .............. A61B 6/482

OTHER PUBLICATIONS

Yao L. et al., "Direct Energy-Resolving CT Imaging Via Energy-Integrating CT Images Using a Unified Generative Adversarial Network", arxiv.org, Cornell University Library, 201 Olin Library Cornell University Ithaca, NY 14853, Oct. 14, 2019, XP081512786.
Clark D.P. et al., "Spectral Data Completion for Dual-Source X-Ray CT", Proceedings of SPIE 10948, Medical Imaging 2019: Physics of Medical Imaging, vol. 10948, Mar. 2019.
Willwmink M.J. et al., "Photon-Counting CT: Technical Principles and Clinical Prospects", Radiology, vol. 289, No. 2, pp. 293-312, Nov. 2018.
Leng S. et al., "Photon-Counting Detector CT: System Design and Clinical Applications of an Emerging Technology", RadioGraphics, vol. 39, No. 3, pp. 729-743, 2019.
Chen H. et al., "Low-Dose CT Via Convolutional Neural Network", Biomedical Optics Express, vol. 8, No. 2, pp. 679-694, Feb. 2017.
Hsieh J. et al., "Computed Tomography: Principles, Design, Artifacts, and Recent Advances", Third Edition, SPIE, Bellingham, vol. PM259, Chapter 3—Section 3.6.3-3.6.4 and Chapter 8—Section 8.3, 2015.
Alvarez R. E. et al., "Energy-Selective Reconstructions in X-Ray Computerized Tomography", Physics in Medicine & Biology, vol. 21, No. 5, pp. 733-744, Sep. 1976.
Johnson T. R. C. Johnson et al., "Dual-Energy CT: General Principles", American Journal of Roentgenology, vol. 199, No. 5, pp. S3-S8, Nov. 2012.
McCollough C. H. et al., "Dual- and Multi-Energy CT: Principles, Technical Approaches, and Clinical Applications", Radiology, vol. 276, No. 3, pp. 637-653, 2015.
Roessl E. et al., "K-Edge Imaging in X-Ray Computed Tomography Using Multi-Bin Photon Counting Detectors", PEM, Physics in Medicine & Biology, vol. 52, No. 15, pp. 4679-4696, 2007.
Roessl E. et al., "Sensitivity of Photon-Counting Based K-Edge Imaging in X-Ray Computed Tomography", IEEE Transactions on Medical Imaging, vol. 30, No. 9, pp. 1678-1690, 2011.
Chen L. C. et al., "DeepLab: Semantic Image Segmentation with Deep Convolutional Nets, Atrous Convolution, and Fully Connected CRFs", IEEE Transactions on Pattern Analysis and Machine Intelligence, 2018.
Ronneberger O. et al., "U-Net: Convolutional Networks for Biomedical Image Segmentation", MICCAI 2015, Part III, LNCS 9351, pp. 234-241, 2015.
Goodfellow I. J. et al., "Generative Adversarial Networks", Part of Advances in Neural Information Processing Systems 27 (NIPS 2014).
H. Hetterich et al., "Phase-Contrast CT: Qualitative and Quantitative Evaluation of Atherosclerotic Carotid Artery Plaque," Radiology, RSNA, vol. 271, No. 3, 870-878, Jun. 2014.

\* cited by examiner

APPARATUS FOR GENERATING PHOTON COUNTING SPECTRAL IMAGE DATA

FIELD OF THE INVENTION

The present invention relates to an apparatus for generating photon counting spectral image data, as well as to an imaging system.

BACKGROUND OF THE INVENTION

A traditional computed tomography (CT) scanner generally includes an x-ray tube mounted on a rotatable gantry opposite a detector array including one or more rows of detector pixels. The x-ray tube rotates around an examination region located between the x-ray tube and the detector array, and emits polychromatic radiation that traverses the examination region and an object or subject disposed therein. The detector array detects radiation that traverses the examination region and generates projection data indicative of the examination region and the object or subject disposed therein. A reconstructor processes the projection data and generates volumetric image data indicative of the examination region and the object or subject disposed therein. The volumetric image data can be processed to generate one or more images that include the scanned portion of the object or subject. The resulting image(s) includes pixels that typically are represented in terms of gray scale values corresponding to relative radio density. Such information reflects the attenuation characteristics of the scanned subject and/or object, and generally shows structure such as anatomical structures within a patient, physical structures within an inanimate object, and the like. The detected radiation also includes spectral information, as the absorption of the radiation by the subject and/or object is dependent on the energy of the x-rays. This spectral information can provide additional information such as information indicative of the elemental or material composition (e.g., atomic number) of the tissue and/or material of the subject and/or object. However, with such a scanner the projection data does not reflect the spectral characteristics as the signal output by the detector array is proportional to the energy fluence integrated over the energy spectrum. As such the resultant data are in effect monochromatic.

Therefore, a development of such a traditional CT approach is to acquire spectral data. Thus, a computed tomography scanner configured for spectral imaging (a spectral scanner) leverages this spectral information to provide further information indicative of elemental or material composition. One approach includes using two X-ray tubes, each emitting an X-ray beam having a different energy spectrum. Another approach includes fast kVp switching in which the voltage across the tube is switched between two different voltages such that measurements at two energies are taken. Another approach includes a multi-layer indirect conversion detector with an uppermost layer that detects lower energy X-rays and a bottommost layer that detects higher energy X-ray. Such spectral data, is here termed non-photon counting X-ray spectral data.

The output of such a spectral scanner, which can be a dual energy scanner acquiring data at two X-ray energies, can be two images one at a high X-ray energy and one at a lower X-ray energy.

However, the mass attenuation coefficient of a material used to reconstruct computed tomography images in effect integrates several physical phenomena affecting the attenuation of the material to x-ray photons. These phenomena include the photoelectric effect, Compton scattering, k-edge effect. See for example: J. Hsieh, *Computed Tomography: Principles, Design, Artifacts, and Recent Advances*. SPIE, 2015. Thus, the non-photon counting spectral data can also be processed utilizing the two attenuation values acquired concurrently at two photon energies to solve for photoelectric effect and Compton scattering basis components. As any two linearly independent sums of two basis functions span the entire attenuation coefficient space, any material can be represented by a linear combination of two basis materials. The basis material components can be used to produce a Compton scattering image and a photoelectric image.

Thus, a dual energy CT system utilizes two attenuation values acquired at two different photon energies to solve for the photoelectric effect and the Compton scattering, while ignoring other component(s) (e.g., one or more K-edge) contributions of the mass attenuation coefficient of a material. See for example: R. E. Alvarez and A. MacOvski, "Energy-selective reconstructions in X-ray computerized tomography," *Phys. Med. Biol.*, 1976. The dual energy approach allows for reconstruction of a high x-ray energy image and a low x-ray energy image, or a Compton scattering image and a photoelectric image. However, the basis functions can also be used to determine virtual monochromatic images, iodine concentration maps, virtual non-contrast images, etc., as well conventional CT images. This allows for reconstruction of virtual monochromatic images, iodine concentration maps, virtual non-contrast images, etc., as well conventional CT images. Several studies have already demonstrated the potential of spectral CT to better characterize human anatomy and function. See for example: T. R. C. Johnson, "Dual-Energy CT: General Principles," *Am. J. Roentgenol.*, vol. 199, no. 5 supplement, pp. S3-S8, November 2012, and C. H. McCollough, S. Leng, L. Yu, and J. G. Fletcher, "Dual- and Multi-Energy CT: Principles, Technical Approaches, and Clinical Applications," *Radiology*, vol. 276, no. 3, pp. 637-653, 2015.

This scheme is well suited for materials such as iodine that has k-edge energy close to the mean value of a diagnostic energy range. Therefore, a linear combination of the two measurements at the low and high regimes of the energy range can represent the material. In more complex cases, in which more accurate material quantification is required, or multiple materials with different k-edge energy are present, the dual-energy approach can result in a sub-optimal result due to its inability to differentiate between materials with different k-edge energies.

Photon-counting CT systems have been developed using direct conversion detector technology to acquire data at multiple energy levels. This provides the potential to allow a more detailed quantification of the different x-ray interactions including the k-edge energy component rather than the being limited to an approximation model that consists solely of the photoelectric effect and the Compton scattering. See for example: E. Roessl and R. Proksa, "K-edge imaging in x-ray computed tomography using multi-bin photon counting detectors," *Phys. Med. Biol.*, 2007, and E. Roessl, B. Brendel, K. J. Engel, J. P. Schlomka, A. Thran, and R. Proksa, "Sensitivity of photon-counting based K-Edge Imaging in X-ray computed tomography," *IEEE Trans. Med. Imaging*, 2011.

Such photon counting systems have the following advantages:
Improved SNR with respect to integrating detectors
Dose reduction (reduced electronic noise)
Improved tissue differentiation/material labeling
Improved quantitative imaging with CT Enabling novel imaging techniques, e.g., K-edge imaging
Reduction of beam hardening artifacts Further, More advanced CT technologies such as the phase-contrast imaging may have improved sensitivity at reduced doses. See for example: H. Hetterich et al., "Phase-Contrast CT: Qualitative and Quantitative Evaluation of Atherosclerotic Carotid Artery Plaque," *Radiology*, 2014.

Therefore, advanced CT systems incorporating photon-counting detectors in a CT system are considered as a technique to better characterize human anatomy and function with multiple clinical applications. The Photon-counting CT systems utilize direct conversion detector technology with complex reconstruction algorithms to leverage multiple attenuation values acquired at multiple different photon energies to solve for the various components contributions to the overall mass attenuation coefficient of a material. Further detail can be found in for example: M. J. Willemink et al: Photon-counting CT: Technical Principles and Clinical Prospects, Radiology 2018, 00, 1-20, and S. Leng et al: Photon-counting Detector CT: System Design and Clinical Applications of an emerging Technology, RadioGraphics, 2019, 39, 729-743. Data acquired from such photon counting system is here termed photon counting x-ray spectral data, and can refer to the raw data prior to its processing into relevant images or relate to the processed data resulting in image data.

However, the complexity of these systems, the requirement of special imaging protocols, and their very high price, has hampered their adoption by clinical users.

There is a need to address these issues.

SUMMARY OF THE INVENTION

It would be advantageous to have improved means of providing photon counting x-ray spectral data. The object of the present invention is solved with the subject matter of the independent claims, wherein further embodiments are incorporated in the dependent claims. It should be noted that the following described aspects and examples of the invention apply also to the apparatus for generating photon counting spectral data, and the imaging system.

In a first aspect, there is provided an apparatus for generating photon counting spectral image data, comprising:
an input unit;
a processing unit; and
an output unit.

The input unit is configured to receive non-photon counting X-ray spectral energy data. The processing unit is configured to implement a deep learning regression algorithm to generate photon counting X-ray spectral data. The generation of the photon counting X-ray spectral data comprises utilization of the non-photon counting X-ray spectral energy data. The output unit is configured to output the photon counting X-ray spectral data.

In an example, the non-photon counting X-ray spectral energy data comprises non-photon counting image data or non-photon counting image data is generated from the non-photon counting X-ray spectral data image data. The non-photon counting image data can comprise a first spectral image at a first X-ray energy and a second spectral image at a second X-ray energy. The photon counting X-ray spectral data can comprise at least one photon counting spectral image.

In an example, the non-photon counting X-ray energy data comprises non-photon counting image data or wherein non-photon counting image data is generated from the non-photon counting X-ray spectral data image data. The non-photon counting image data can comprise a Compton scattering image and a photoelectric image. The photon counting X-ray spectral data can comprise at least one photon counting spectral image.

In an example, the processing unit is configured to implement a reconstructor to process the non-photon counting X-ray spectral data to generate the non-photon counting image data.

In an example, the at least one photon counting spectral image comprises one or more photon counting spectral images from a group including: a photon counting image at the first X-ray energy, a photon counting image at the second X-ray energy, a photon counting Compton image, a photon counting photoelectric image, a photon counting virtual monochromatic image, a photon counting contrast agent quantitative image, a photon counting non-contrast image, a photon counting cancellation image, a photon counting Iodine image, a photon counting k-edge image.

In an example, the input unit is configured to receive reconstruction parameters employed by a reconstructor to generate the non-photon counting image data. The generation of the photon counting X-ray spectral data can comprise utilization of the reconstruction parameters.

In an example, the input unit is configured to receive acquisition parameters employed by an image acquisition unit to acquire the non-photon counting X-ray spectral energy data. The generation of the photon counting X-ray spectral data can comprise utilization of the acquisition parameters.

In an example, the input unit is configured to receive patient parameters of a patient from whom the non-photon counting X-ray spectral energy data was acquired by an image acquisition unit. The generation of the photon counting X-ray spectral data can comprise utilization of the patient parameters.

In an example, the input unit is configured to receive reference non-photon counting X-ray spectral data and reference photon counting X-ray spectral data. The processing unit is configured to train the deep learning regression algorithm comprising utilization of the reference non-photon counting X-ray spectral data and the reference photon counting X-ray spectral data.

In an example, the reference non-photon counting X-ray spectral data comprises reference non-photon counting image data. The input unit is configured to receive the reconstruction parameters employed to generate the reference non-photon counting image data. The training of the deep learning regression algorithm can comprise utilization of the reconstruction parameters.

In an example, the reference photon counting X-ray spectral data can comprise image data.

In an example, the input unit is configured to receive acquisition parameters employed by one or more image acquisition units to acquire the reference non-photon counting X-ray spectral energy data. The training of the deep learning regression algorithm can comprise utilization of the acquisition parameters.

In an example, the input unit is configured to receive patient parameters of at least one patient from whom the reference non-photon counting X-ray spectral energy data was acquired by one or more image acquisition units. The training of the deep learning regression algorithm can comprise utilization of the patient parameters.

In a second aspect, there is provided an imaging system, comprising:
an image acquisition unit; and
an apparatus according to the first aspect.

The image acquisition unit is configured to acquire non-photon counting X-ray spectral data and provide the non-photon counting X-ray spectral data to the input unit of the apparatus.

In an example, the processing unit of the apparatus is configured to implement a reconstructor to process the non-photon counting X-ray spectral data to generate non-photon counting image data.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
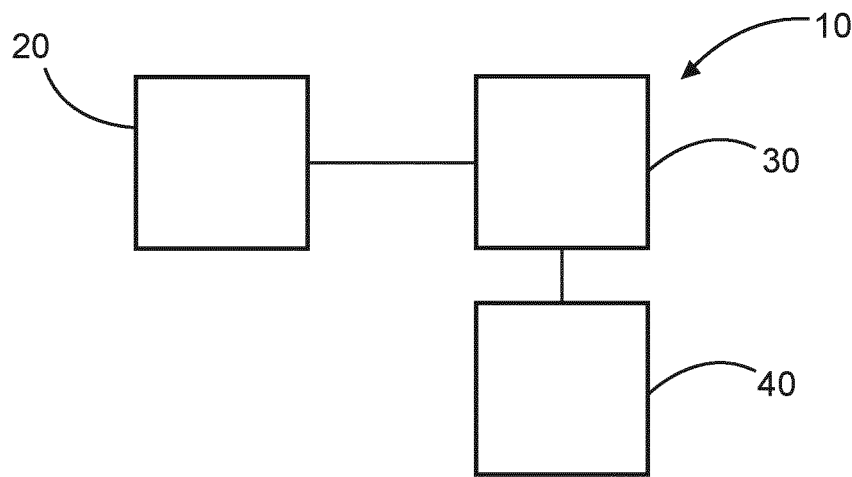
FIG. 1 shows an example of an apparatus for generating photon counting spectral image data.

FIG. 1 shows an example of an apparatus 10 for generating photon counting spectral image data. The apparatus comprises an input unit 20, a processing unit 30, and an output unit 40. The input unit is configured to receive non-photon counting X-ray spectral energy data. The processing unit is configured to implement a deep learning regression algorithm to generate photon counting X-ray spectral data. The generation of the photon counting X-ray spectral data comprises utilization of the non-photon counting X-ray spectral energy data. The output unit is configured to output the photon counting X-ray spectral data.

According to an example, the non-photon counting X-ray spectral energy data comprises non-photon counting image data or non-photon counting image data is generated from the non-photon counting X-ray spectral data image data. The non-photon counting image data, whether comprised within the non-photon counting X-ray spectral energy data or generated from the non-photon counting X-ray spectral energy data, can comprise a first spectral image at a first X-ray energy and a second spectral image at a second X-ray energy. The photon counting X-ray spectral data can comprise at least one photon counting spectral image.

According to an example, the non-photon counting X-ray energy data comprises non-photon counting image data or non-photon counting image data is generated from the non-photon counting X-ray spectral data image data. The non-photon counting image data, whether comprised within the non-photon counting X-ray spectral energy data or generated from the non-photon counting X-ray spectral energy data, can comprise a Compton scattering image and a photoelectric image. The photon counting X-ray spectral data can comprise at least one photon counting spectral image.

According to an example, the processing unit is configured to implement a reconstructor to process the non-photon counting X-ray spectral data to generate the non-photon counting image data.

According to an example, the at least one photon counting spectral image comprises one or more photon counting spectral images from a group including: a photon counting image at the first X-ray energy, a photon counting image at the second X-ray energy, a photon counting Compton image, a photon counting photoelectric image, a photon counting virtual monochromatic image, a photon counting contrast agent quantitative image, a photon counting non-contrast image, a photon counting cancellation image, a photon counting Iodine image, a photon counting k-edge image.

According to an example, the input unit is configured to receive reconstruction parameters employed by a reconstructor to generate the non-photon counting image data. The generation of the photon counting X-ray spectral data can comprise utilization of the reconstruction parameters.

According to an example, the input unit is configured to receive acquisition parameters employed by an image acquisition unit to acquire the non-photon counting X-ray spectral energy data. The generation of the photon counting X-ray spectral data can comprise utilization of the acquisition parameters.

According to an example, the input unit is configured to receive patient parameters of a patient from whom the non-photon counting X-ray spectral energy data was acquired by an image acquisition unit. The generation of the photon counting X-ray spectral data can comprise utilization of the patient parameters.

According to an example, the input unit is configured to receive reference non-photon counting X-ray spectral data and reference photon counting X-ray spectral data. The processing unit is configured to train the deep learning regression algorithm comprising utilization of the reference non-photon counting X-ray spectral data and the reference photon counting X-ray spectral data.

The reference non-photon counting X-ray spectral data can be the same type of non-photon counting X-ray spectral data that the processing unit utilizes to generated photon counting X-ray spectral data.

The reference photon counting X-ray spectral data can be the same type of photon counting X-ray spectral data generated by the processing unit.

In an example, the reference non-photon counting X-ray spectral data comprises at least one reference non-photon counting spectral image.

In an example, the reference photon counting X-ray spectral data comprises at least one reference photon counting spectral image.

In an example, the at least one reference photon counting spectral image comprises one or more photon counting spectral images from a group including: a photon counting image at the first X-ray energy, a photon counting image at the second X-ray energy, a photon counting Compton image, a photon counting photoelectric image, a photon counting virtual monochromatic image, a photon counting contrast agent quantitative image, a photon counting non-contrast image, a photon counting cancellation image, a photon counting Iodine image, a photon counting k-edge image.

According to an example, the reference non-photon counting X-ray spectral data comprises reference non-photon counting image data. The input unit is configured to receive the reconstruction parameters employed to generate the reference non-photon counting image data. The training of the deep learning regression algorithm can comprise utilization of the reconstruction parameters.

According to an example, the reference photon counting X-ray spectral data comprises image data.

According to an example, the input unit is configured to receive acquisition parameters employed by one or more image acquisition units to acquire the reference non-photon counting X-ray spectral energy data. The training of the deep learning regression algorithm can comprise utilization of the acquisition parameters.

According to an example, the input unit is configured to receive patient parameters of at least one patient from whom the reference non-photon counting X-ray spectral energy data was acquired by one or more image acquisition units. The training of the deep learning regression algorithm can comprise utilization of the patient parameters.

Figure 2:
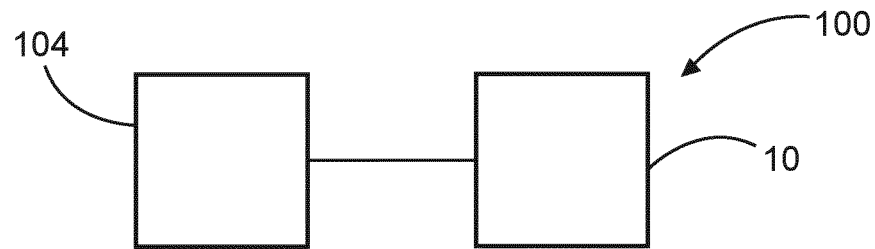
FIG. 2 shows an example of an imaging system for generating photon counting spectral image data.

FIG. 2 shows an example of an imaging system 100. The imaging system comprises an image acquisition unit 104, and an apparatus 10 for generating photon counting spectral image data as described with respect to FIG. 1. The image acquisition unit is configured to acquire non-photon counting X-ray spectral data and provide the non-photon counting X-ray spectral data to the input unit of the apparatus.

According to an example, the processing unit of the apparatus is configured to implement a reconstructor to process the non-photon counting X-ray spectral data to generate non-photon counting image data.

Thus, a photon-counting CT system is provided that can deliver photon-counting results from dual energy CT data acquisition hardware and protocols that do not involve acquiring photon counting data. In this way complex and expensive hardware based photon-counting CT system are not required to produce the photon-counting CT results. The system uses a deep learning regression approach to provide the photon-counting CT results from the dual energy CT data, the acquisition protocol and reconstruction parameters. The deep learning regression model leverages the inter-voxel local statistics within the input data to predict the photon-counting results from the dual energy CT data.

The apparatus for generating photon counting spectral image data, and the imaging system for generating photon counting spectral image data are now described in more specific detail where reference is made to FIGS. 3-6.

Figure 3:
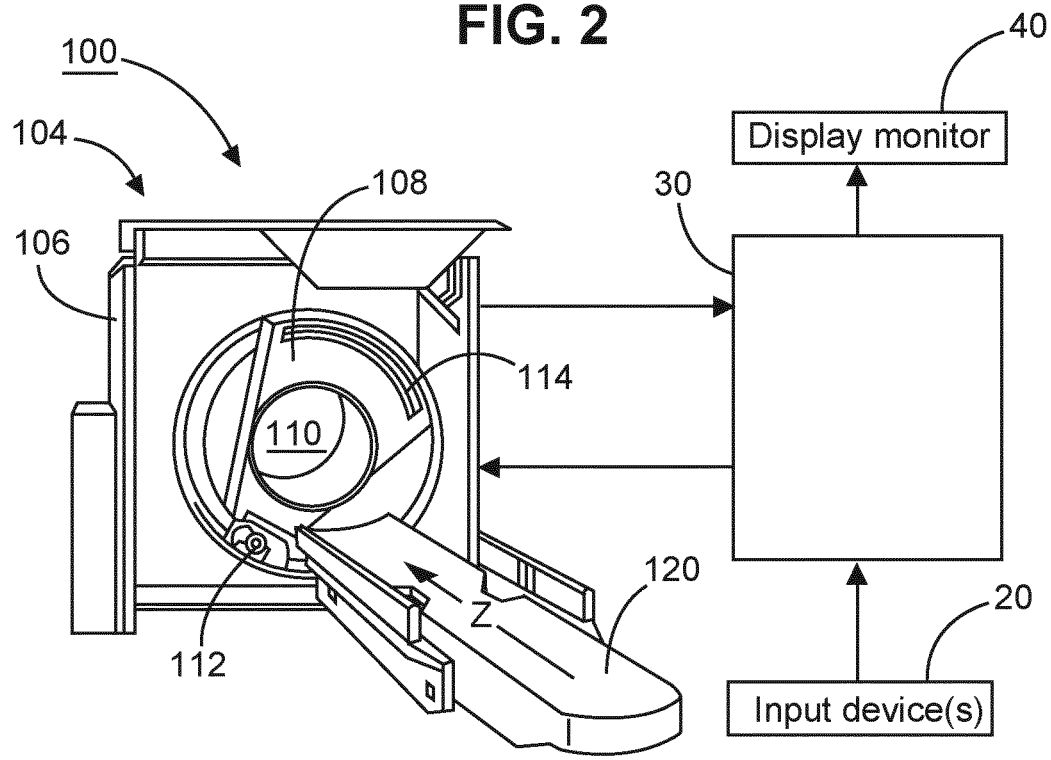
FIG. 3 shows a detailed example of an imaging system for generating photon counting spectral image data.

FIG. 3 shows a detailed example of an imaging system 100 for generating photon counting spectral image data. An image acquisition system 104 is shown, such as a spectral CT scanner that does not acquire photon counting data, but acquires spectral data as described previously through utilization of two x-ray tubes, fast switching of an x-ray tube between different voltages, or a detector acquiring data relating to low-energy x-ray photons in one layer and acquiring data relating to high-energy x-ray photons in a second layer. The image acquisition unit 104 includes a generally stationary gantry 106 and a rotating gantry 108, which is rotatably supported by the stationary gantry 106 and rotates around an examination region 110 about a z-axis. The radiation source or sources 112, is/are rotatably supported by the rotating gantry 108, and rotates with the rotating gantry 108, and emits radiation that traverses the examination region 110.

A radiation sensitive detector array 114, which an example could be the two layer detector discussed above, subtends an angular arc opposite the radiation source(s) 112 across the examination region 110. The illustrated radiation sensitive detector array 114 includes one or more rows of layer indirect conversion detector elements (e.g., scintillator/photo-sensor). The array 114 detects radiation traversing the examination region 110 and generates projection data (line integrals) indicative thereof.

Thus at this time non-photon counting spectral data has been acquired by the image acquisition unit 104.

This non-photon counting spectral data can be provided directly to the processing unit 30. However, the non-photon counting spectral data can first be passed to a reconstructor, that generates for example a high-energy x-ray photon image and a low energy x-ray photon image, or basis images as discussed above such as a Compton scattering image and photoelectric image, and then these non-photon counting spectral images can be provided to the processing unit 30.

The processing unit 30 then receives data via an input unit 20 relating to the acquisition parameters of the image acquisition unit 104 in acquiring the non-photon counting spectral data, along with patient parameters. The processing unit 30 can itself then reconstruct the non-photon counting spectral data itself into non-photon counting spectral images and use the parameters that form part of a reconstruction along with the acquisition parameters and patient parameters in order to determine photon counting spectral data such as image data from the non-photon counting spectral images. Or, if the processing unit is provided with the already reconstructed non-photon counting spectral images then the input unit is provided with the reconstruction parameters used in the reconstruction, and the reconstruction parameters are again used with the acquisition parameters and patient parameters to determine photon counting spectral data such as images from the non-photon counting spectral images. The resultant photon counting spectral images can then be presented for example on output unit 40 such as a display monitor, and/or provided to a storage medium for saving as digital data.

Thus, it is clear that the processing unit 30 can operate separately to the image acquisition unit and in effect be an off-line apparatus that takes already acquired non-photon counting spectral data or images and generates photon counting spectral data or images from that data, or the processing unit 30 can be intrinsically linked to a non-photon counting spectral image acquisition unit that in a cost-effective manner can produce photon counting spectral data or images in real time.

Thus, a new advanced CT system is presented that does not require specialized hardware or new imaging protocols beyond standard dual-energy CT data. The system leverages the inter-voxel statistics of dual energy CT data to predict the advanced CT results, such as the photon-counting results by using a deep-learning regression model. This is described in more detail below with respect to FIGS. 4-6.

Advantages of the New System Include:

A Cost effective system, that does not require any dedicated photon-counting acquisition hardware.

A seamless integration that allows the clinicians to use their regular clinical acquisition protocols.

Output images similar to real photon counting images that exhibit reduced noise in the images, due to in effect a removal of detector electronic noise because the photon counting results can discount or reject such detector noise.

The system can operate in one of two configurations. In the first configuration, the dual-energy data used for input consists of two images acquired at different energy levels: low and high, and the output is photon-counting images from N different energy bins. Thus, Photon-counting images can be generated that can be presented at higher resolution of energy levels, for example 5 rather than 2 in the dual-energy input data.

In the second configuration, the dual-energy data used for input consists of two-basis images, such as photo-electric image and Compton scattering image, and the output Photon-counting data consists of the Photon-counting CT results including, but not limited to, photon counting Photo-electric image, photon counting Compton scattering image, and the photon counting k-edge energy image.

Figure 4:
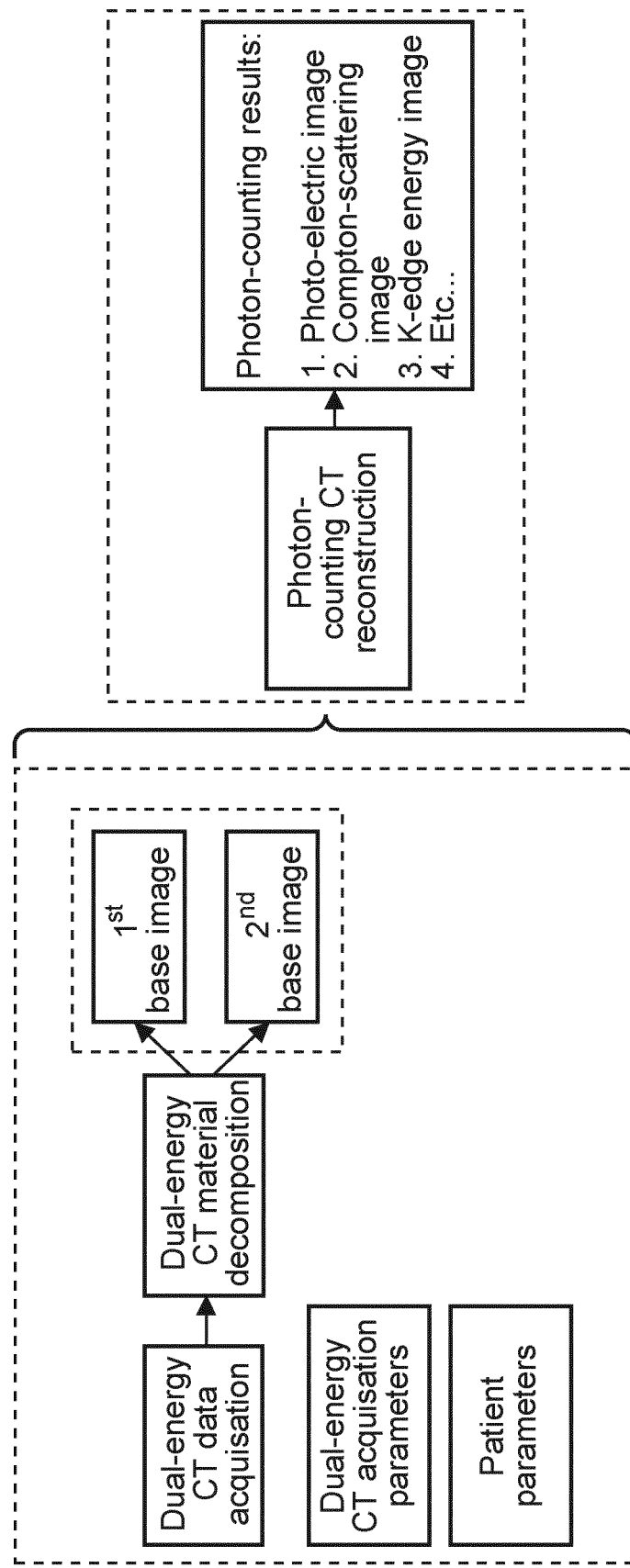
FIG. 4 shows in detail functional elements of an exemplar imaging system for generating photon counting spectral image data.

FIG. 4 shows in detail functional elements of an exemplar imaging system for generating photon counting spectral image data. The system has the following main components:

Dual-energy CT data. The spectral data should include at least images/projection data having at least two energy levels that allow spectral analysis along with acquisition and reconstruction parameters including the scan type, body part, mA, mAs, kVp, rotation time, collimation, pitch, reconstruction filter, reconstruction algorithm, slice thickness, slice increment, matrix size and field of view among others, and patient parameters such as body weight, age, sex, clinical tests results, among others Photon-counting reconstruction module implemented within a processing unit.

A. Dual-Enemy CT Data

The data used as input to the system should include at least CT data with at least two energy levels that allow spectral analysis. Examples include, but are not limited to, CT images of the anatomy of interest reconstructed from CT projection data acquired with dual-layer detector system that separates the x-ray flux at the detector into two levels of energy.

B. Photon-Counting CT Reconstruction

The input to this module includes, but is not limited to, the scan protocol, the acquisition parameters, and the dual-energy CT data. The input can optionally include the dual-energy CT results generated using the conventional dual-energy CT pipeline. The module reconstructs the Photon-counting results from the input data, and potentially additional acquisition and patient parameters, using a deep-neural regression network trained to predict the Photon-counting results from the input data during a training procedure.

The Photon-counting reconstruction module may include an addition pre-processing step such as applying a de-noising algorithm to reduce the noise in the input data and improve overall performance.

Figure 5:
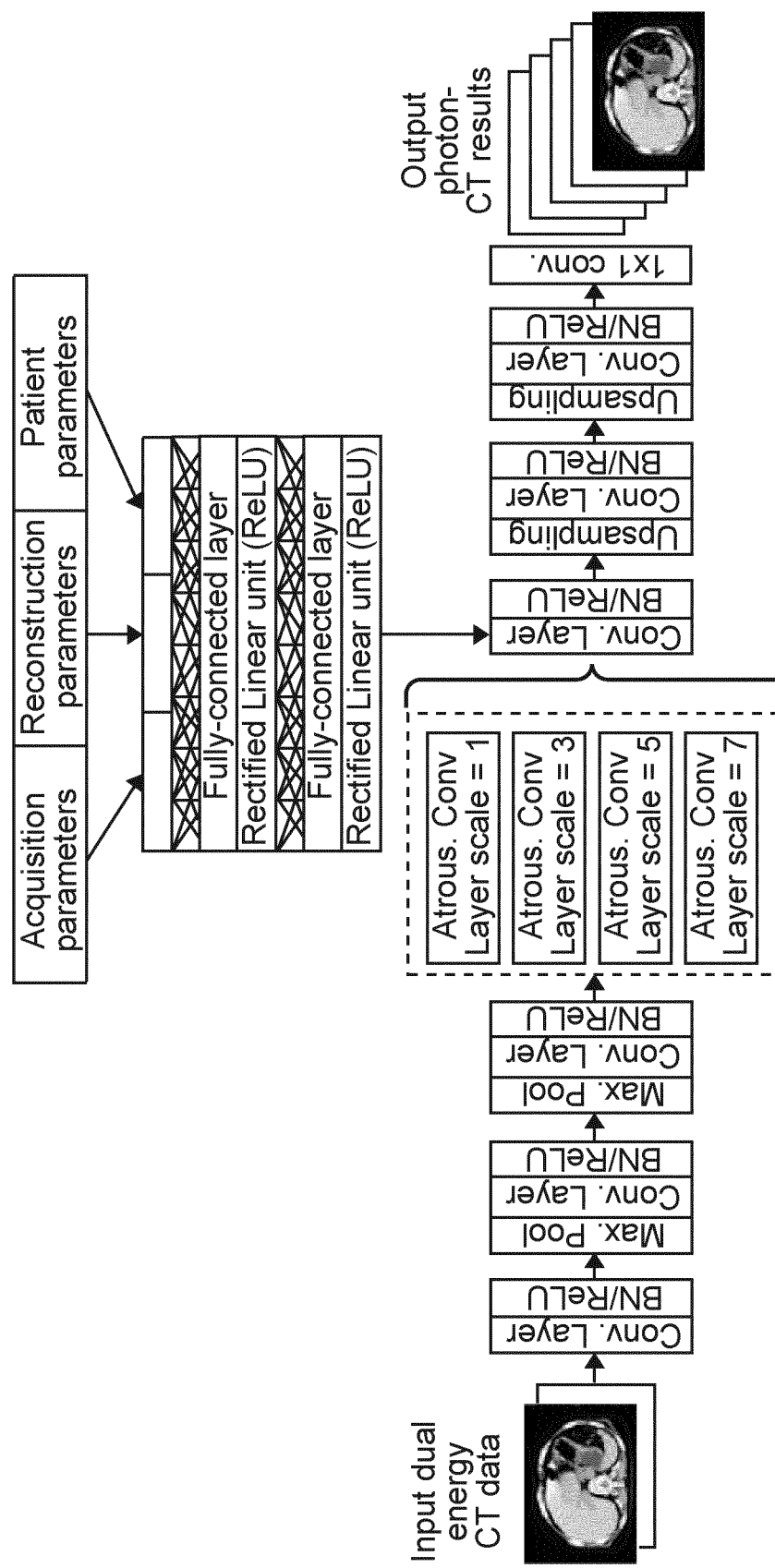
FIG. 5 shows a detailed representation of an exemplar deep multi-scale neural network using Atrous convolutions for photon counting reconstruction.
Figure 6:
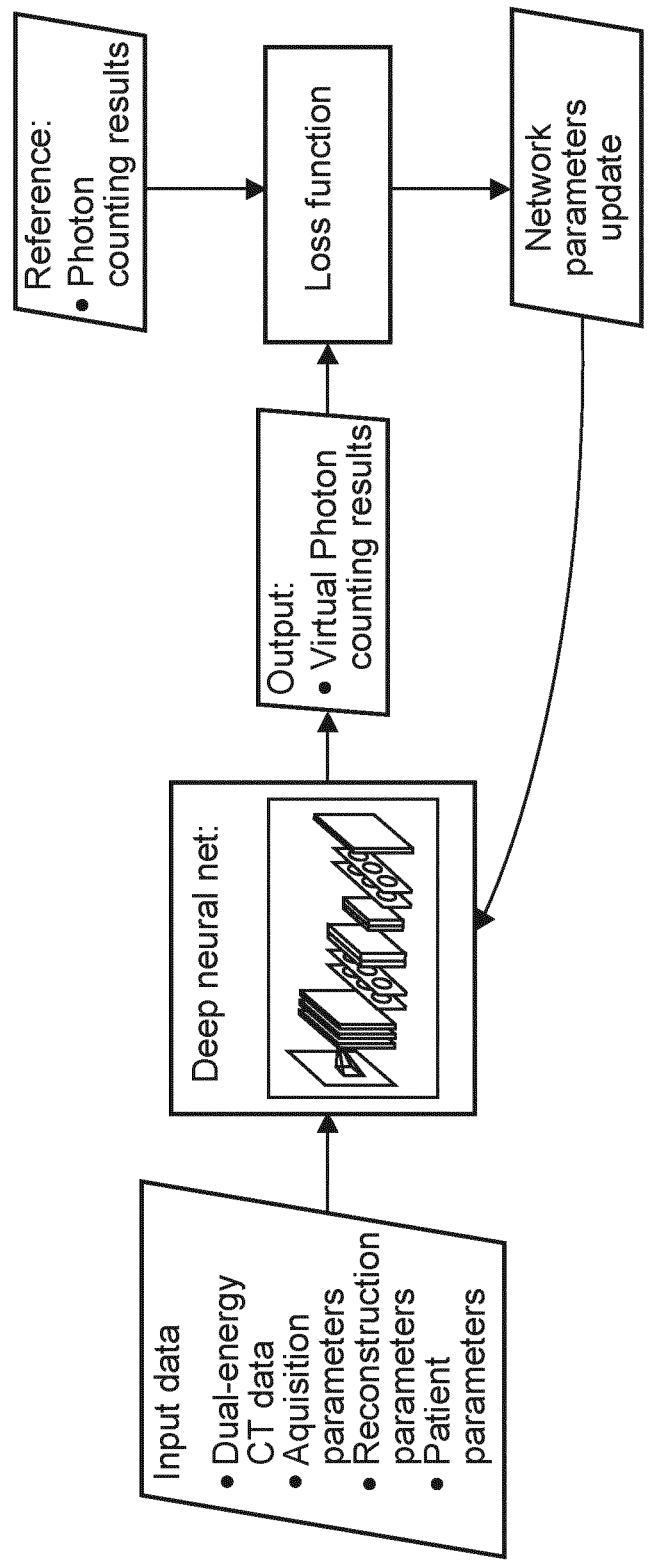
FIG. 6 shows a detailed representation of workflow representing training of an exemplar deep multi-scale neural network for photon counting reconstruction.

The photon counting reconstruction is described in more detail with respect to FIGS. 5-6.

FIG. 5 presents an architecture for the deep neural regression network for virtual Photon-counting CT. A deep multi-scale neural network using Atrous convolutions for the photon counting reconstruction module. For more information on Atrous convolutions see for example: L. C. Chen, G. Papandreou, I. Kokkinos, K. Murphy, and A. L. Yuille, "DeepLab: Semantic Image Segmentation with Deep Convolutional Nets, Atrous Convolution, and Fully Connected CRFs," *IEEE Trans. Pattern Anal. Mach. Intell.,* 2018. Additional potential architectures can include the U-net architecture among others. For more detail on U-net architectures, see for Example: O. Ronneberger, P. Fischer, and T. Brox, "U-Net: Convolutional Networks for Biomedical Image Segmentation," *Miccai,* 2015.

The input to the neural network is the dual energy CT data, including at least low and high energy images or two-base images. The network applied several convolutional layers. Each layer is composed of several convolution kernels along with some activation functions such as the rectified linear units and a max-pooling layer, which reduce the size of the images by down-sampling. The output of this first part of the neural (shown on the left side) is served as input to additional Atrous convolutional layers that apply convolutions with varying receptive fields on the input. The results of this component are then combined with the acquisition model parameters (top component) network, such as acquisition parameters, reconstructions parameters and patient parameters. At this stage this is all combined together as a linear combination, followed by a rectified linear unit activation function. Finally, both components are combined together through a set of convolutional layers followed by up-sampling layer to increase image size back to its original size. The output is then the generated photon-counting images.

Continuing with FIG. 5, and in specific detail. In this figure a described above an example of a deep regression network is shown. The network consists of the flowing layers, where concatenation is provided to different channels of the output of networks 1 and 2:

Network 1 (Input: Dual Energy CT):

The dual energy CT data is input, as shown on the left hand side of FIG. 5.

The following layer is a convolutional layer with a batch normalization Transform (BN), and rectifier activation function (ReLU). For more information on ReLU see for example: https://en.wikipedia.org/wiki/Activation_function The following layer comprises Max pooling, with another convolutional layer with a batch normalization Transform, and rectifier activation function;

The following layer also comprises Max pooling, with another convolutional layer with a batch normalization Transform, and rectifier activation function;

Then shown within the dashed box, concatenation of the output of the following parallel layers is provided, where the input for the following layers is the output of the operator in Max pooling:

1—Atrous/Dilated Convolution
   3—Atrous/Dilated Convolution
   5—Atrous/Dilated Convolution
   7—Atrous/Dilated Convolution For more detail on Atrous/Dilated convolution see for example: F. Yu and V. Koulton: Multi-Scale Context Aggregation By Dilated Convolutions, published as a conference paper at ICLR 2016.

Network 2 (Input: Parameters Acquisition Parameters, Reconstructions Parameters, Patient Parameters):

Concatenation of all input parameters is conducted

The next layer is a fully connected network and rectifier activation function (ReLU);

The next layer is again a fully connected network and rectifier activation function;

Combination of Networks 1 and 2

The outputs from networks 1 and 2 is combined in parallel channels and are provided to a convolutional layer followed by BN and a rectifier activation function;

The next layer is a convolutional layer, with a batch normalization Transform, and rectifier activation function;

The next layer comprises upsampling, which is upscaling of an image by factor 2 using for example NN/Bilinear/cubic interpolation;

The next layer is a convolutional layer, with a batch normalization Transform, and rectifier activation function;

The Next Layer Comprises Upsampling

The next layer is a convolutional layer, with a batch normalization Transform, and rectifier activation function;

Finally Convolution is carried out with a 1×1 kernel with one output channel, the output of which is the photon counting spectral image data/image.

The inventors have also assessed how to reduce the noise in the resultant photon counting spectral images, and determined that this operation can be carried out itself using a deep regression network—see for example: H. Chem et al: Low-dose CT via convolutional neural network, Biomedical Optics Express, vol. 8, No. 2, 679-694 (2017).

FIG. 6 shows a training procedure for the network used in the Photon-counting reconstruction module of FIG. 5. FIG. 6 shows a photon counting reconstruction module, deep neural regression network training procedure. The training procedure aims to determine the parameters (i.e. convolutional kernels, etc) of the network described in FIG. 5. The procedure initializes the network parameters with some random values, and then modifies them using a gradient decent or a similar algorithm according to the pre-defined loss function, which can be in this case the root mean squared error between the predicted photon-counting images and the reference photon-counting images. Other loss functions can be utilized.

Formally, the goal of the training procedure is to find a function: $f(CT_{DE}) \rightarrow CT_{PC}$ that maps the input Dual-energy CT data $(CT_{DE})$ to the photon-counting CT data $CT_{PC}$.

The training is done by minimizing some loss function:

$$\hat{f} = \arg\min_{f} D(f(CT_{DE}), CT_{PC})$$

Where D represents the loss function. A potential example of D is the root mean-squared error as discussed above:

$$D(f(CT_{DE}), CT_{PC}) = \|f(CT_{DE}), CT_{PC}\|^2$$

Thus, FIG. 6 shows a training session of a supervised deep network. The training could be done using one of the common optimization algorithms, for example: D. P. Kingma and J. L. Ba, ADAM: A METHOD FOR STOCHASTIC OPTIMIZATION, published as a conference paper at ICLR 2015.

In addition, an hybrid adversarial training procedure in which the goal of the training is to both to achieve lower RMSE for samples with reference hardware-based photon-counting results and to increase the number of images produced by the network to be classified as hardware-based photon counting results can be carried out. This can be carried out by an adversarial trainer for samples without reference hardware-based photon counting results. An example of an appropriate adversarial trainer can be found here: I. J. Goodfellow et al., "Generative Adversarial Networks," June 2014.

It has to be noted that embodiments of the invention are described with reference to different subject matters. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for generating photon counting spectral image data, comprising:
   a memory that stores a plurality of instructions; and
   a processor coupled to the memory and configured to execute the plurality of instructions to:
   receive non-photon counting X-ray spectral energy data that comprises non-photon counting image data, wherein the non-photon counting image data comprises a first spectral image at a first X-ray energy and a second spectral image at a second X-ray energy;
   implement a deep learning regression algorithm to generate photon counting X-ray spectral data using the non-photon counting X-ray spectral energy data; and
   output the photon counting X-ray spectral data.

2. The apparatus according to claim 1, and wherein the photon counting X-ray spectral data comprises at least one photon counting spectral image.

3. The apparatus according to claim 2, wherein the at least one photon counting spectral image comprises one or more photon counting spectral images from a group including: a photon counting image at the first X-ray energy, a photon counting image at the second X-ray energy, a photon counting Compton image, a photon counting photoelectric image, a photon counting virtual monochromatic image, a photon counting contrast agent quantitative image, a photon counting non-contrast image, a photon counting cancellation image, a photon counting Iodine image, a photon counting k-edge image.

4. The apparatus according to claim 2, wherein the processor is configured to receive reconstruction parameters employed by a reconstructor to generate the non-photon counting image data, and wherein generation of the photon counting X-ray spectral data comprises utilization of the reconstruction parameters.

5. The apparatus according to claim 1, wherein the non-photon counting image data comprises a Compton scattering image and a photoelectric image, and wherein the photon counting X-ray spectral data comprises at least one photon counting spectral image.

6. The apparatus according to claim 1, wherein the processor is configured to receive acquisition parameters to acquire the non-photon counting X-ray spectral energy data, and wherein generation of the photon counting X-ray spectral data comprises utilization of the acquisition parameters.

7. The apparatus according to claim 1, wherein the processor is configured to receive patient parameters of a patient from whom the non-photon counting X-ray spectral energy data was acquired, and wherein generation of the photon counting X-ray spectral data comprises utilization of the patient parameters.

8. The apparatus according to claim 1, wherein the processor is configured to receive reference non-photon counting X-ray spectral data and reference photon counting X-ray spectral data, and wherein the processor is configured to train the deep learning regression algorithm comprising utilization of the reference non-photon counting X-ray spectral data and the reference photon counting X-ray spectral data.

9. The apparatus according to claim 8, wherein the reference non-photon counting X-ray spectral data comprises reference non-photon counting image data, and wherein the processor configured to receive the reconstruction parameters employed to generate the reference non-photon counting image data, and wherein training of the deep learning regression algorithm comprises utilization of the reconstruction parameters.

10. The apparatus according to claim 8, wherein the reference photon counting X-ray spectral data comprises image data.

11. The apparatus according to claim 8, wherein the processor is configured to receive acquisition parameters to acquire the reference non-photon counting X-ray spectral energy data, and wherein training of the deep learning regression algorithm comprises utilization of the acquisition parameters.

12. The apparatus according to claim 8, wherein the processor is configured to receive patient parameters of at least one patient from whom the reference non-photon counting X-ray spectral energy data, and wherein training of the deep learning regression algorithm comprises utilization of the patient parameters.

13. A computer implemented method for generating photon counting spectral image data, comprising:
  receiving non-photon counting X-ray spectral energy data that comprises non-photon counting image data, wherein the non-photon counting image data comprises a first spectral image at a first X-ray energy and a second spectral image at a second X-ray energy;
  implementing a deep learning regression algorithm to generate photon counting X-ray spectral data using the non-photon counting X-ray spectral energy data; and
  outputting the photon counting X-ray spectral data.

14. A non-transitory computer readable medium comprising executable instructions which, when executed by at least one processor, cause the at least one processor to perform a method for generating photon counting spectral image data, the method comprising:
  receiving non-photon counting X-ray spectral energy data that comprises non-photon counting image data, wherein the non-photon counting image data comprises a first spectral image at a first X-ray energy and a second spectral image at a second X-ray energy;
  implementing a deep learning regression algorithm to generate photon counting X-ray spectral data using the non-photon counting X-ray spectral energy data; and
  outputting the photon counting X-ray spectral data.

* * * * *